United States Patent [19]
Chandler et al.

[11] Patent Number: 6,093,150
[45] Date of Patent: Jul. 25, 2000

[54] ULTRASOUND OTOSCOPE

[75] Inventors: Paul E. Chandler, Santa Cruz; John W. Sliwa, Los Altos; Joan C. Main, Mountain View; Worth B. Walters, Cupertino, all of Calif.

[73] Assignee: Acuson Corporation, Mountain View, Calif.

[21] Appl. No.: 09/001,389

[22] Filed: Dec. 31, 1997

[51] Int. Cl.[7] ..................................................... A61B 8/00
[52] U.S. Cl. ......................................................... 600/459
[58] Field of Search ................................... 600/437, 459, 600/466, 467, 461, 463

[56] References Cited

U.S. PATENT DOCUMENTS

| | | | |
|---|---|---|---|
| 5,174,296 | 12/1992 | Wantanabe et al. | 600/463 |
| 5,255,681 | 10/1993 | Ishimura et al. | |
| 5,335,663 | 8/1994 | Oakley et al. | |
| 5,385,147 | 1/1995 | Anderson et al. | |
| 5,398,689 | 3/1995 | Connor et al. | |
| 5,419,334 | 5/1995 | Miyagawa . | |
| 5,438,997 | 8/1995 | Sieben et al. | |
| 5,447,075 | 9/1995 | Hockaday . | |
| 5,469,853 | 11/1995 | Law et al. | |
| 5,474,075 | 12/1995 | Goldberg et al. | |
| 5,482,047 | 1/1996 | Nordgren et al. | 128/662.03 |
| 5,546,947 | 8/1996 | Yagami et al. | |
| 5,617,865 | 4/1997 | Palczewska et al. | |
| 5,680,863 | 10/1997 | Hossack et al. | |

OTHER PUBLICATIONS

N. Yanagihara et al. "Pneumolabyrinth in perilymphatic fistula: report of three cases.". Am J Otol 1987 Jul.;8(4):313–318.

D. S. Poe et al. "Evaluation of Perilymphatice Fistulas by Middle Ear Endoscopy". *The American Journal of Otology*/ vol. 13, No. 6: pp. 529–533, Nov. 1992.

L. S. Alvord et al. "Real–time B–scan Ultrasound in Middle Ear Assessment". *The American Institute of Ultrasound in Medicine, J Ultrasound Med 9*: pp. 91–94, 1990.

D. S. Poe et al. "Comparison of Endoscopic and Surgical Explorations for Perilymphatic Fistulas". *The American Journal of Otology*/vol. 15, No. 6: pp. 735–738, Nov. 1994.

L. S. Alvord. "Uses of ultrasound in audiology.". *J Am Acad Audiol* 1990 Oct;1(4):227–235.

*Primary Examiner*—Marvin M. Lateef
*Assistant Examiner*—Maulin Patel
*Attorney, Agent, or Firm*—Brinks Hofer Gilson & Lione

[57] ABSTRACT

An ultrasonic imaging device for imaging the middle and inner ear is here described. It includes a thin, flattened shaft, a deformable support structure, a mounting surface, and an ultrasonic imaging array. Imaging is effected by the introduction of an acoustically conductive fluid into the middle ear space. Access to the tympanum through the external auditory canal and adjacent to the probe shaft for the purpose of injecting fluid into the middle ear space both before and during the exam is permitted by the flattened probe shaft. The deformable probe shaft may be bent or angulated to best fit a particular patients ear thus permitting optimal access for imaging through the tympanum and around the manubrium of the malleus attached down the midline of the tympanum. High resolution imaging of all structures within the middle and inner ear is achievable.

32 Claims, 4 Drawing Sheets

ULTRASOUND OTOSCOPE

FIELD OF THE INVENTION

This invention relates generally to the field of ultrasound imaging and more particularly to an ultrasound otoscope for middle and inner ear imaging. It relates to a method and device to achieve a detailed, real-time image of the middle and inner ear through an intact tympanum.

PRIOR ART

Visual examination of middle and inner ear structures are limited by the translucent tympanum (the ear drum). The inability to see within the middle ear limits detection of, for example, perilymphatic fistulas (holes through the round or oval windows into the perilymph filled spaces of the inner ear) and otosclerosis (a disease where growth of spongy bone gradually obstructs the oval window and causes progressively increasing deafness). Visual examination of the inner ear is further limited by the round and oval window membranes and the dense bone surrounding the rest of the inner ear.

Perilymphatic fistulas are suspected whenever patients experience sudden hearing loss or vertigo. Perilymphatic fistulas must also be ruled out before diagnosing a patient with Meniere's disease. Visualization of the perilymph immediately beyond the round and oval windows may permit detection of small air bubbles pulled into the inner ear through fistulas when middle ear pressure exceeds pressure within the inner ear. No reliable method of detecting perilymphatic fistulas exists to date, although many methods have been tried. Three of the most promising methods are: (1) beta 2-transferrin assays, (2) use of fluorescein dyes, and (3) micro-optical endoscopy.

(1) Beta 2-transferrin is found only in cerebrospinal fluid and perilymph. Thus, analysis of middle ear fluids for the presence of beta 2-transferrin holds promise as an indicator of perilymphatic fistulas if detection methods can be improved.

(2) Use of fluorescein dyes involves injecting fluorescein dye intravenously into the patients blood. The theory is that the dye travels through the blood and eventually enters the perilymph. Perilymph leaking into the middle ear space would then contain fluorescein dye and could be detected due to its fluorescence under ultraviolet illumination. However, it is suggested that fluorescein dye seen in the middle ear space following perilymphatic fistula comes instead from blood entering the middle ear space and not from perilymph. If this is correct, the diagnostic value for fluorescein detection must then be questioned. Incorporated by reference herein is a study to this effect entitled Comparison of Endoscopic and Surgical Explorations for Perilymphatic Fistulas written by Dennis S. Poe, M.D., F.A.C.S. and Ian D. Bottrill, F.R.C.S. in the American Journal of Otology, Volume 15 Number 6, November 1994.

(3) With micro-optical endoscopy, endoscopes are inserted through the tympanum or eustachian tube to optically view the surface of some middle and inner ear structures. Diagnostic success of micro endoscopes has been limited and the results of examinations with these devices are rarely, if ever, used by practicing physicians to alter their diagnosis. Micro-optical endoscopes have been used successfully to detect perilymphatic fistulas created in laboratory animals but have not successfully detected perilymphatic fistulas in patients selected for their high likelihood of having active perilymphatic fistulas. Some disadvantages of the micro-optical endoscope are:

a) A complete exam requires insertion of the endoscope through the tympanum and eustachian tube. Insertion through the tympanum leaves a large perforation that must eventually heal. Insertion through the eustachian tube is difficult, potentially painful for the patient, and can be accomplished only with a lower resolution fiber optic endoscope;

b) The viewing angles offered by the micro-optical endoscope are limited and do not permit viewing of all structures of the middle ear. Viewing access to the round and oval windows can be blocked by adhesions from previous surgeries when rigid endoscopes are used. Furthermore, these endoscopes can see only the surfaces viewable from the middle ear cavity and are incapable of imaging past the surface of the inner ear (unless inserted through and thus rupturing the round or oval window);

c) Insertion of the micro-optical endoscope into the middle ear space frequently causes an increase in fluids within the middle ear. Some important diagnoses, such as the detection of perilymphatic fistulas (detected by an extremely low volume fluid leak from the inner ear) can easily be obscured by this excess fluid.

Without any diagnostic tool to detect suspected perilymphatic fistulas, many patients undergo unnecessary and ineffective perilymphatic fistula repair surgeries for perilymphatic fistulas they do not have. Other patients who do have perilymphatic fistulas, are not giver the benefit of perilymphatic fistula repair surgery that could otherwise restore them to a normal lifestyle.

CT and MRI scans have also been employed to study the middle and inner ear. However, both techniques lack sufficient resolution to detect perilymphatic fistulas. CT and MRI scans are not capable of the detailed imaging required to make many essential diagnosis. Furthermore, CT and MRI scanners image too slowly to permit unaliased imaging of middle and inner ear structures when these structures are driven at frequencies in the audible and near-audible ranges.

Otosclerosis is a disease whereby a growth of spongy bone in the inner ear gradually obstructs the oval window and causes progressively increasing deafness. Currently, otosclerosis is most commonly diagnosed using hearing tests. Micro-optical endoscopes could be used to diagnose otosclerosis but are incapable of quantifying the reduced mobility of the ossicles caused by the otosclerotic deposits.

A-mode and B-mode ultrasound techniques have been used to detect the presence of naturally occurring middle ear fluids in suspected cases of otitis media. Detection is accomplished by acoustic impediography or observation of additional echoes generated at the back surface of middle ear fluids or at middle ear surfaces. These techniques have been implemented with single crystal transducers and mechanical scanners designed for ophthalmic use. The techniques, while useful for the detection and assessment of naturally occurring middle ear fluids, are incapable of high resolution imaging of the middle and inner ear.

There is, therefore, a need for improved means for the detection of perilymphatic fistulas and other conditions of the middle and inner ear and for improved ultrasound probes designed specifically for optimized imaging and motion analysis of the middle and inner ear.

SUMMARY OF THE INVENTION

The present invention is directed to a method and apparatus for detailed imaging of middle and inner ear structures through the intact tympanum. The invention further permits optional real-time assessment of motion of these structures in response to calibrated drive signals having frequencies in the audible, sub-audible, and super-audible ranges.

Disclosed herein is an ultrasound array probe that is insertable into the external auditory canal for the purpose of imaging the middle and inner ear.

In more detail, disclosed herein is an array probe comprised of a probe body having an insertable portion of no more than 8 mm in widest cross-sectional dimension, the probe body having a distal end; and an imaging transducer array attached to the distal end, wherein the probe may be inserted into the external ear for the purpose of imaging the middle and inner ear.

Also disclosed herein is a method for examining the internal and middle ear comprising the steps of:

filling the middle ear cavity with fluid;

placing enough material in the external ear cavity for acoustic coupling;

inserting a probe into the external ear for the purpose of imaging the middle and inner ear, the probe having an imaging array on its distal end and having an insertable cross sectional dimension of no more than about 8 mm.

The ultrasound otoscope in accordance with this invention comprises a shaft, the shaft having a longitudinal axis and being thin enough to fit within an ear alongside a needle or cannula for flooding the middle ear with fluid;

a support structure having a body and a first end connected to the body, the support structure fitting within the shaft, the first end of the support structure providing a mounting surface that is off set from the longitudinal axis; and an ultrasonic imaging array mounted on the mounting surface of the first end of the support structure.

The ultrasound otoscope in accordance with this invention comprises a shaft, the shaft having a longitudinal axis and being thin enough to fit within an ear alongside a needle or cannula for flooding the middle ear with fluid, the shaft being plastically deformable;

a support structure having a body and a first end connected to the body, the support structure fitting within the shaft, the first end of the support structure providing a mounting surface that is off set from the longitudinal axis; and an ultrasonic imaging array mounted on the mounting surface of the first end of the support structure, the array being movable in the azimuthal and elevational directions.

The ultrasound otoscope in accordance with this invention comprises a shaft, the shaft being less than about 8 mm and flattened;

a support structure having a body and a first end, the support structure fitting within the shaft, the first end of the support structure providing a mounting surface;

an ultrasonic imaging array mounted on the mounting surface of the first end of the support structure;

a probe handle connected to the second end of the support structure and shaft; and an electrical cable connecting the array elements to an ultrasound imaging system via conductors contained within the probe shaft and handle.

In one preferred embodiment, a small ultrasonic high frequency imaging array is mounted at the end of a thin flattened probe shaft mounted in the essentially end-fire direction and offset in the elevational direction at the end of the probe shaft. This offset permits the imaging array to slip under the ridge in the anterior wall of the external auditory canal and to the side of the manubrium of the malleus which blocks the acoustic path down the midline of the tympanum of the ear. This offset enables imaging through the tympanum to either side of the manubrium, permitting more complete exploration of the middle and inner ear structures.

In another embodiment, the mounting surface may be attached with a machined swivel joint and may contain control means to permit swiveling in elevation and/or azimuth. Swiveling may be controlled manually from the probe handle or may be controlled automatically by the ultrasound system.

In another embodiment swiveling in the elevation direction may be controlled automatically in order to sweep the two-dimensional image plane scannable with a one-dimensional array to collect data sets for a three-dimensional image.

In another embodiment, three-dimensional data sets may be collected through use of a two-dimensional array of ultrasound elements in place of the one-dimensional array.

Another means of conducting three-dimensional imaging is to automatically swivel a one-dimensional array about its azimuthal axis in the direction of elevation, thus fanning a three-dimensional volume with the two-dimensional image produced from the one-dimensional array.

Another embodiment may also contain a single, low frequency crystal or array transducer for introduction of drive signals in the audible, sub-audible, or super-audible frequency ranges. Synchronization of the drive transducer signal with the imaging array will permit detailed sampling of the periodic motions of middle and inner ear structures induced by drive transducer applied continuous wave, pulsed, and otherwise modulated signals.

In another embodiment, a high power ultrasonic transducer is used for ultrasonic cleaning of middle ear surfaces, ultrasonic cleaning of ossicles, and ultrasound tissue damage and/or removal for the purpose of ultrasound surgery within the middle and inner ear.

In using the ultrasound otoscope, the middle ear space which is normally filled with air at ambient pressure, is flooded with an acoustically conductive viscous fluid, in a pressure sensitive manner so as not to damage the ear and so as to replace the air with the fluid. Once flooded, the middle ear space provides an acoustic path to middle and inner ear structures.

The ultrasound otoscope potentially permits limited study of the structures and motion of structures within the inner ear, such as the organ of Corti. These studies have the potential to advance the diagnosis of many previously undiagnosable diseases and further the scientific community's understanding of the function of the inner ear.

BRIEF DESCRIPTION OF THE DRAWINGS

The following drawings are offered to illustrate aspects of the inventions described herein. They are not to be construed as limitations thereof and are not drawn to scale.

TERMS

In this disclosure, the terms "elevation", "elevational" and "azimuthal" are used. These are common terms in the field of medical ultrasound technology and in the field of radar. The words elevation, and "elevational" are generally understood to mean the distance of something above a point of reference. The term "azimuthal" is generally understood to mean the horizontal angular distance from a reference direction, usually the northern point of the horizon, to the point where a vertical circle through a celestial body intersects the horizon, usually measured clockwise. In the field of ultrasound, the azimuthal dimension is understood to be the dimension containing the elements of a one-dimensional array of elements. This is because this is the dimension where electronic steering and changes in angle can occur. Those involved in the field of medical ultrasound technology define the orientation of a one-dimensional array such that the azimuthal elements are contained along the x axis, the azimuthal and elevation dimensions of the array lie in the x, y plane, and therefore, the dimension of elevation of the elements lie along the y axis. In the absence of electronic steering, an ultrasound beam transmitted from this array will propagate along the z-axis. This is in the x, z plane from the intersection of the x, y, z axes at which a measurement is made or to which an ultrasound beam is electronically steered. For the purposes of this description, the x, y, and z axes are understood to lie along the azimuthal, elevation, and beam axes respectively of the non-steered array. The z dimensions of an array are further defined to lie in the x, y plane with the z axis centered on both dimensions of the array. In this description, when width is discussed, this width lies in the azimuthal plane. When thickness is discussed, this thickness lies in the elevational plane. When a longitudinal axis is mentioned, this refers to length and lies along the z axis.

DETAILED DESCRIPTION OF THE PREFERRED EMBODIMENT

The present invention involves flooding the middle ear space with an acoustically conductive viscous fluid. The fluid is preferably warmed, biocompatible, isotonic, and pH adjusted. Appropriately engineered fluids are mentioned in U.S. Pat. No. 5,335,663 (Oakley, et. al.), and in U.S. Pat. No. 5,469,853 (Law, et. al.) both of which are incorporated herein by reference. The fluids mentioned in these patents are sodium hyaluronates.

Transducer probes discussed in the Oakley and Law patents are designed to permit oozing of viscous fluids into the region surrounding the imaging array within the cavity in which the transducer probe has been inserted for the purpose of providing acoustic coupling between the imaging transducer and the tissue to be imaged. In the current invention, the viscous fluid is injected into a body cavity into which the transducer probe and its imaging transducer cannot be inserted, for the purpose of re-engineering the acoustic properties of the body cavity to support propagation of ultrasonic waves between the imaging transducer and the tissue to be imaged through an otherwise air-filled body cavity that cannot support ultrasonic waves in its native state.

The fluids are used differently in the present methodology than in the Oakley and Law patents. In the present methodology, the fluid is injected into an air-filled cavity. A probe is then used to image through the cavity from outside the cavity, using a little more of the fluid to acoustically couple the probe to the membrane surrounding the cavity and through which the cavity is imaged.

Flooding of the middle ear air space with fluid can be accomplished with a hypodermic needle or cannula inserted through the tympanum. Alternatively, a cannula can be inserted just distal to the tympanum through the tissues of the external auditory canal and directed with the aid of a curved trocar, into the air space of the middle ear just proximal to the tympanum. The fluid will eventually be absorbed by the tissues of the middle ear or allowed to escape through the eustachian tube some time after the examination is concluded. Or, it may be withdrawn at the end of the examination through a drain channel built into the cannula or through use of a second hypodermic needle, the first needle providing a means for air to re-enter the middle ear during fluid withdrawal and thus preventing creation of reduced pressure within the middle ear. Once flooded, the middle ear space provides an acoustic path to middle and inner ear structures. At this time, an ultrasound otoscope (100) as herein described may be placed in the ear.

Figure 1A:
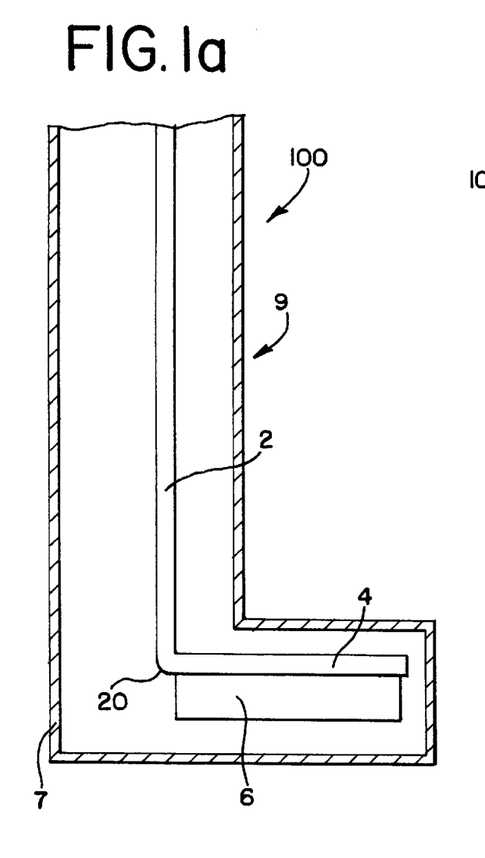
FIG. 1a is a partially sectional side view of the otoscope of this invention with an offset ultrasound imaging array.
Figure 1B:
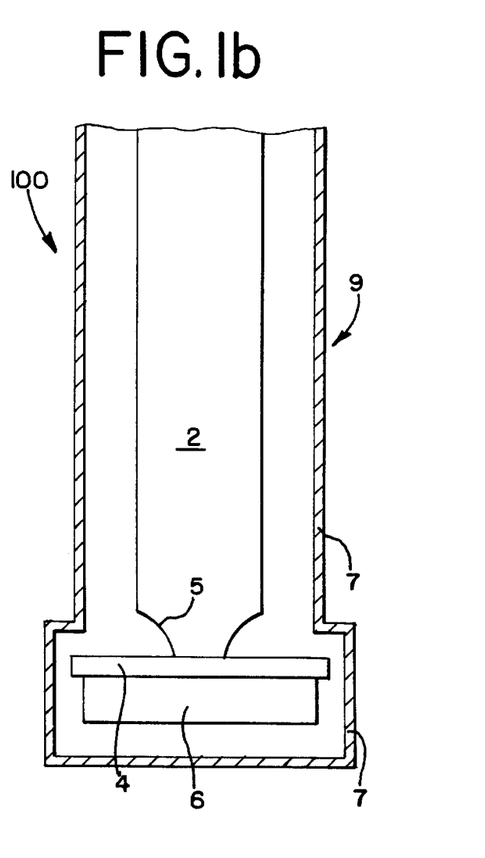
FIG. 1b is a diagrammatic front view of FIG. 1a exhibiting the necked-down portion of the device.
Figures 2A, 2B, 2C, 3A, 3B, 3C:
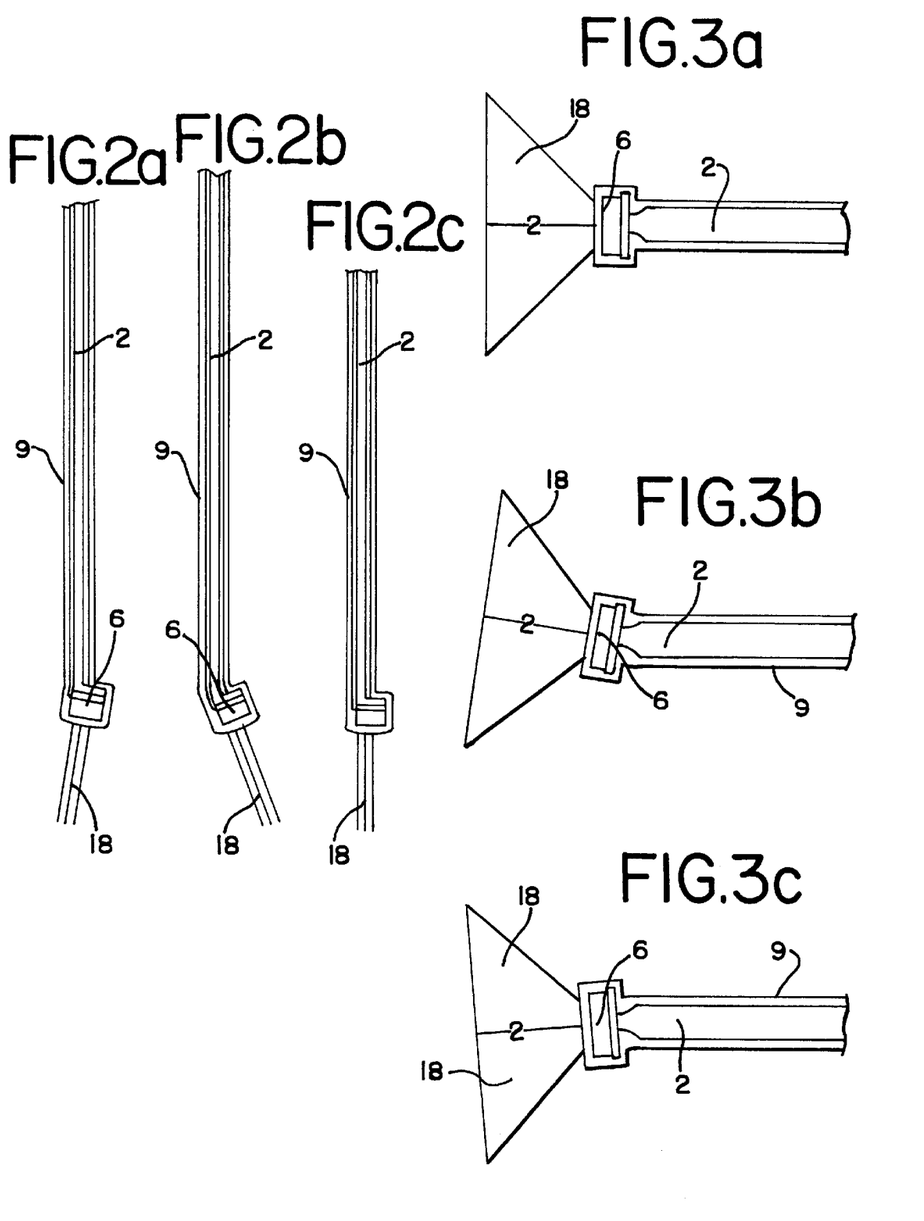
FIGS. 2a, 2b, and 2c are diagrammatic side views of the probe, envelope and array with the array moved into various different elevational positions.
FIGS. 3a, 3b, and 3c are front views of the devices of FIGS. 2a, 2b, and 2c with the array moved into various different azimuthal positions.

FIGS. 1a, 1b, and 4a through 4d show the ultrasound otoscope probe (100) of the invention. It is comprised of a generally upside down T shaped housing (7), as seen in FIG. 1b, which forms an outside flexible envelope which contains a lens and that surrounds and hermetically seals therein interconnect circuits (3), an imaging array (6) and an elongated deformable support (2). The longitudinal body of the T forms a shaft (9) portion of the probe which extends to an unshown handle portion. Deformable support (2) bends or angles at bend (20) thereby giving it an L shaped appearance as seen in FIG. 1a. The foot of the L acts as a mounting surface (4) on which is mounted the high frequency imaging array (6) comprised of a plurality of transducer elements for imaging. The leg of the L which is generally perpendicular to mounting surface (4), is situated parallel so and within shaft (9) of probe (100).

Because of the L shape of deformable support (2), imaging array (6) is seen as mounted off-center of the central longitudinal axis of shaft (9) of ultrasound otoscope probe (100). This positioning permits imaging around the manubrium of the malleus which is attached to the inner surface of the tympanum along a line extending from the center of the tympanum to a point on its circumference. Otoscope probe (100) is connected, through its handle via an electrical cable and connector (not shown), to a high performance and fully capable ultrasound imaging system (not shown), like the Acuson Sequoia System, for minimally permitting B-mode imaging, Doppler and quantitative assessment of the middle and inner ear. High frequency B-mode imaging with the ultrasound otoscope (100) is ideally suited for the detection of perilymphatic fistulas by the smoke-like (when aqueous flooding fluids are used) or bead-like (when non-aqueous flooding fluids are used) image produced at the interface of the homogeneous viscous fluid used to flood the middle ear space and water-like perilymph leaking from the fistula. The ultrasound otoscope probe (100) is most ideally suited to detect air bubbles within the inner ear just behind the round or oval windows that may occur when higher pressures in the middle ear push air into the inner ear through a fistula.

Imaging array (6) may be mounted at a fixed elevational angle within housing (7) or the elevational angle may be adjustable permitting fanning in elevation for better 2D image plane selection or 3D data set acquisition. Further, it may be mounted at a fixed rotation angle about a perpendicular to the array surface or it may be rotatable for better 2D image plane selection. Imaging array (6) may be planar or curved. It may be a 2D array, taking advantage of the very short acoustic propagation distances and fixed position or periodic nature of many of the structures to be imaged to permit synthetic aperture techniques or some of its variants to be employed. Its azimuthal dimension may be from about 4 mm to about 10 mm, its elevational dimension from about 1 mm to about 4 mm, and its operating frequency from about 5 MHz to about 20 MHz. Many such arrays are sold by Acuson Corporation and are familiar to those skilled in the art. The center of the elevation dimension of the imaging array (6) may be offset in the elevational direction from the central longitudinal axis of the probe shaft to any offset distance contained in the range of about 25% to about 300% of the elevation aperture width. Generally, the offset should be such as to permit the imaging array (6) to slip under the ridge in the external auditory canal and to the side of the manubrium of the malleus which blocks the acoustic path down the midline of the tympanum. This permits more complete imaging of the middle and inner ear through the tympanum to both sides of the manubrium.

Offset adjustment herein is contemplated by bending of the deformable probe (100) for differing ear configurations. This is possible due to the materials used in making the probe such that it is plastically deformable. There is no need for additional offset means. With the deformability of the probe (100), the design is set to a nominally useful position for all patients and then can be gently adjusted to better match a particular patient's ear and provide optimal imaging by enhancing the position of the imaging array (6) and orientation within the ear.

Specifically, both lateral and angular displacements of the probe can be achieved by deformations of the probe. For example, putting a "z" shaped kink in shaft (9) would provide a lateral displacement of array (6). Rotating array (6) at bend (20) would cause mostly an angular displacement of array (6), and placing a gentle curvature in shaft (9) would cause both lateral and angular displacement of array (6). Probes with end-fire ultrasonic-arrays are known in the art. Some swivel in elevation. These designs, however, are not offset. The prior art appears to be devoid of intercavity probes that swivel in elevation as well as probes that are offset in elevation. Therefore, prior art probes are not as needed for use within the external auditory canal.

Probe shaft (9) surrounds both deformable support (2) and interconnect circuits (3). In the area where deformable support (2) bends (20) to form mounting surface (4) for imaging array (6), there are defined notches or a narrowed portion (5). The material for housing (7) is compliant so as to bend, compress, and stretch as needed when deformable support (2) is bent. Narrowed portion (5) facilitates this bending in a limited fashion in the azimuthal direction. Some of the materials out of which deformable support (2) may be made are shape memory materials such as metal alloys. These enable one to mold and remold the shape without resulting high fatigue is the material. In this way the probe may be plastically deformed and reshaped as needed.

Interconnect circuits (3) comprise a flex circuit such as found in U.S Pat. No. 5,398,689 (Hewlett-Packard Company) incorporated herein by reference. Flex circuits are typically made of a dielectric material such as polyimide film with copper traces lithographically etched there into from copper layers bonded to the dielectric material. Traces are copper wires left when the copper layer is lithographically etched to remove all other copper. These traces are bonded to the dielectric material and therefore held in place by the dielectric material. Such circuits include hot leads and, ground lead(s). A copper shield is typically placed around the transducer and flex circuit of a probe to protect them from radio frequency interference (RFI) from outside electrical noise sources and may be partly incorporated into the design of the flex circuit.

In the present invention, the flex circuit (3) is preferably bonded to support shaft (2), during manufacture before putting support shaft (2) in its hermetic envelope housing (7). All components would preferably be built on support shaft (2), including the flex circuit, transducer, backing block, ground and shield connections, matching layers if used, and lens if made from a different material than the rest of the envelope housing (7). The envelope housing (7) is then cast around these elements and array (6) and bonded to the handle of otoscope probe (100).

It is important to protect the flex circuit (3) from tearing, this being a possibility when considering bending probe (100). Accordingly, protection of the flex circuit (3) in this invention is accomplished by bonding it to deformable support (2) and narrowing the conductors near notches or narrowing (5) to limit the total tension placed on flex circuit traces as the probe is bent, particularly near narrowing (5). Accordingly, notches, narrowings of any type, or a very thin probe (100) are all acceptable means to resolve this problem as each causes a smaller contact region to exist with the mounting surface (4) for the array (6). Forming otoscope probe (100) as a thin rod is preferable as it eliminates the need for narrowings (5).

Bend (20) and notch (5) may be replaced with a machined swivel joint to extend the life of otoscope probe (100). Otoscope probe (100) may then contain control means to permit swiveling in elevation and/or azimuth from the proximal handle portion of otoscope (100). That proximal handle portion is the portion remaining outside the ear and easily accessible to the operator. Swiveling may be controlled manually from the handle or may be controlled automatically by the ultrasound system. A control system permitting angulation of the probe tip for better contact with the tympanum may be used.

Figure 4A:
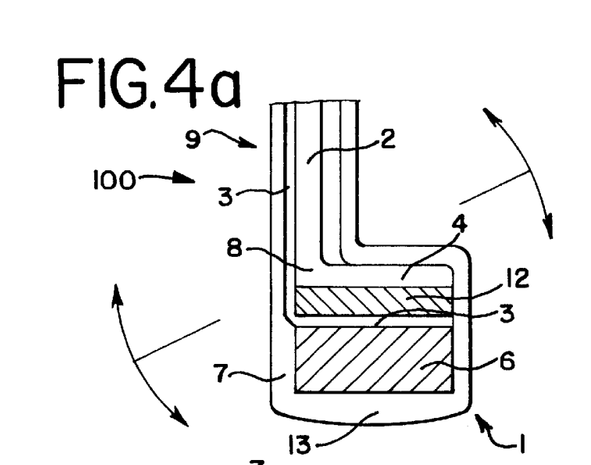
FIGS. 4a through 4d are more detailed views of the distal array end of the otoscope of the previous figures with FIG. 4a being side view, 4b a back view, 4c a bottom view, looking into the array face, and 4d a front view.

Reference numeral (8) in FIG. 4a represents the nominal center of rotation in the direction of elevation when probe (100) is bent near imaging array (6). Reference numeral (10) in FIG. 4b, represents the nominal center of rotation in the azimuthal direction of otoscope (100) in the area of imaging array (6) when probe (100) is bent near imaging array (6).

FIGS. 2a through 2c and 3a through 3c demonstrate several possible scan plane orientations (18) relative to the orientation of probe (100) made possible by the ability to deform the probe (100) and its internal components in the azimuthal and elevational directions.

In another embodiment, three-dimensional data sets may be collected through use of a two-dimensional array of ultrasound elements in place of the one-dimensional array (6) shown in the figures herein. A two-dimensional array can take advantage of the short acoustic propagation distances and fixed positions of the structures to be imaged, thereby permitting synthetic aperture techniques or some of its variants to be employed.

Figure 4B:
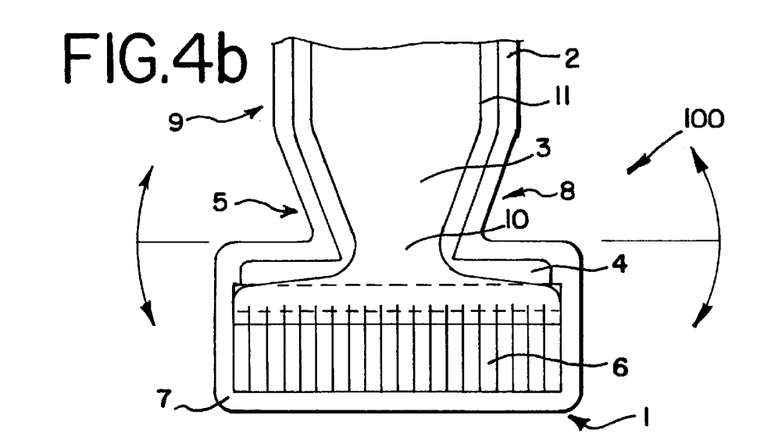
Figure 4C:
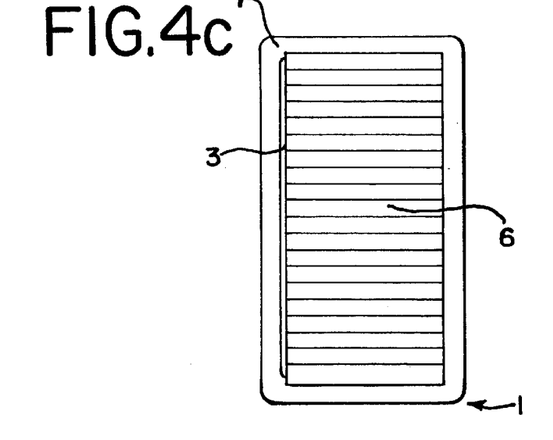
Figure 4D:
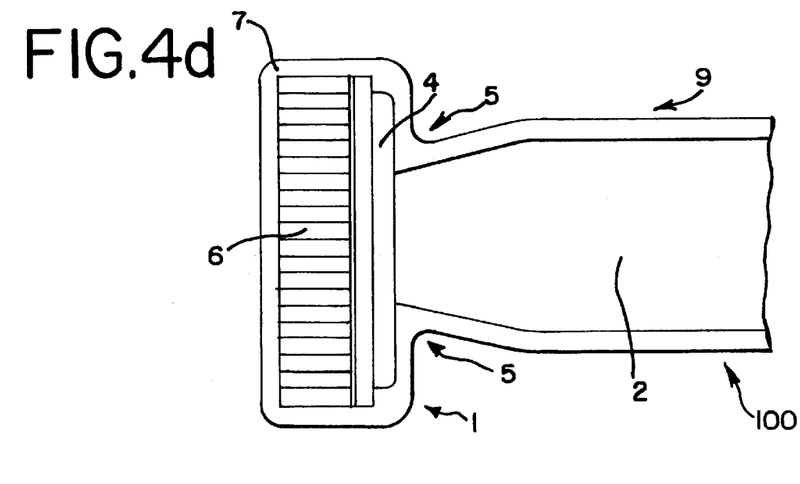

Trace (11), shown in FIG. 4b, represents a single trace of an interconnect flex circuit (3) used in ultrasound devices. There is one such trace for every transducer element used to make signal connections and preferably, but not required, one additional trace for every transducer element used to make ground connections. As noted above, traces (11) are bonded to support 2 and especially designed to limit excessive tension that would cause them to fatigue and fail as support (2) is bent. Only the outer two traces (11) connected to the end transducer elements have been shown in FIG. 4b for the sake of simplicity and these have been shown in the same plane. When all traces are shown, they are preferably of controlled thickness and spacing as they course through the necked-down region of deformable support (2) near the center of rotation (10). The traces are preferably of controlled thickness and spacing as they neck down and until they fan out again on deformable support (2) so as to provide desirable transmission line characteristics as known to those skilled in the art.

Reference numeral (12) in FIG. 4a is an acoustical backing block used to suppress ultrasound moving in the backward direction. Reference numeral (13) in FIG. 4a represents the hermetic seal. Housing (7) contains hermetically sealed therein a lens which may or may not be made of the same material as housing (7). Lenses are typically made of, for example, (room temperature vulcanized) RTV silicon rubber with various filler compounds added to adjust acoustic properties. The same materials can be used to form a hermetic seal. Preferably the lens formed in housing (7) and housing (7) are of the same material. However, contemplated within this invention is that the materials may as well be different. The lens must meet specific acoustic properties, one of which is sound velocity within the material. This greatly limits the materials that may be selected and therefore, it may be desirable to make the lens of one material and the remainder of housing (7) of another material. The requirements of the housing (7) generally include electrically isolating the conductive components of the probe from the patient to prevent electrical injury to the patient and flexibility to bend with deformable support (2).

Probe (100) in the area of shaft (9), is thin, may be flattened, hemispherical or otherwise shaped, and is plastically deformable to hold its position when bent. In terms of the word thin, otoscope probe (100) in the area of shaft (9) should be wide enough to contain the deformable support (2) and interconnect circuits. Shaft (9) must accommodate all of this, insulating layers, and be sufficiently thick to provide electrical safety to the patient and protect the probe from environmental effects such as saline and disinfecting solutions. On the other hand, otoscope probe (100) must be thin enough in the area of shaft (9) to permit access along its side opposite the offset direction of the imaging array (6) to permit clear access for about 30 gauge up to about 12 gauge hypodermic needles or up to 6 french catheters for the injection of fluid into the middle ear. These constraints require a shaft (9) having a thickness of between about 2 mm and about 6 mm and a width less than about 8 mm. About 8 mm is the maximum width that shaft (9) can have for it to fit into an ear and be easily manipulated. The thinner and narrower shaft (9) is the better as long as it maintains its pushability and sufficient stiffness while being deformable to permit the probe to be bent into needed positions. Shaft (9) should be capable of being bent to wrap around corners while the distal end of the otoscope probe (100) is angulated to optimally steer the imaging plane. This bending would be accomplished outside the ear before inserting otoscope probe (100). Otoscope probe (100) should not deform further under the normal forces applied during imaging and while it is inserted in the ear.

There are many ways to make a shaft (9) including deformable support (2) to meet the above criteria. Shaft (9) could be made as a thin wire if appropriate interconnect electrical elements (3) are used. With the flex circuits currently available, if the signal and ground traces are laid parallel to one another to enable a flattened shaft (9), the probe shaft is then thicker in one dimension than the other so that it appears flat. This shaping accommodates both the circuitry and provides an ergonomic grip as it extends into the proximal or handle portion of otoscope probe (100). This permits the operator to easily rotate the transducer probe (100) about the central axis of the shaft (9) without slipping. A shaft (9) of this design will have a widest dimension of between about 3 mm to about 8 mm and a narrowest dimension in the range of about 2 mm to 6 mm.

Figure 5A:
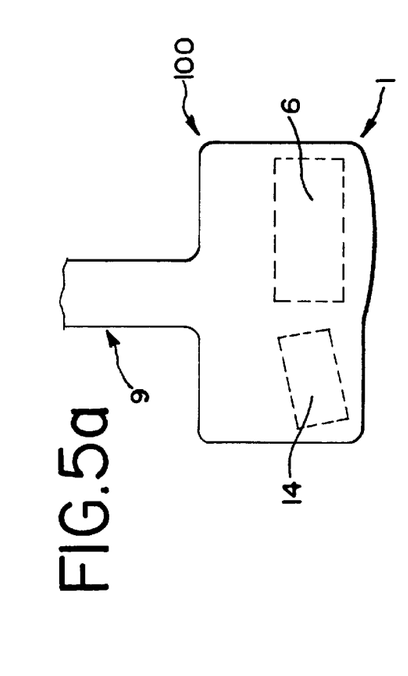
FIGS. 5a, 5b, and 5c are diagrammatic side, bottom, and front views respectively of the distal end of the otoscope of the invention with an optionally included drive transducer included.
Figure 5B:
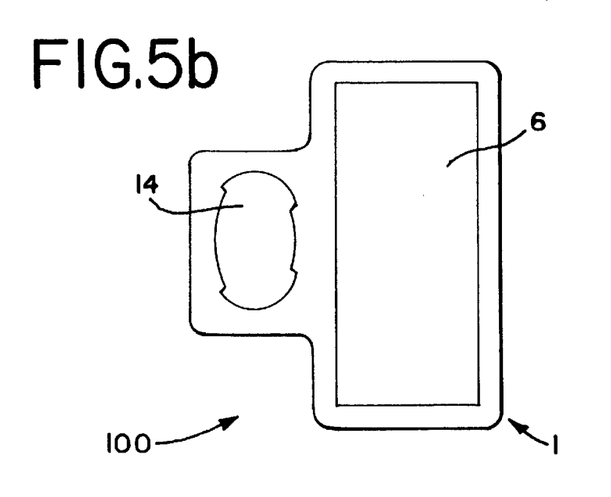
Figure 5C:
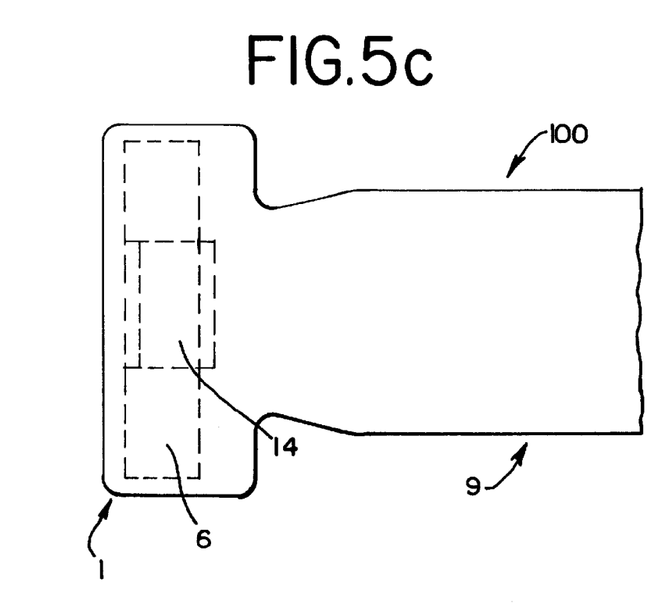

As seen in FIGS. 5a, 5b and 5c, otoscope probe (100) may also include a low frequency single crystal or array transducer (14) for introduction of driving signals. The transducer (14) is mounted in the essentially end-fire direction. That is the beam will be emitted from the end of the device rather than the sides. The optionally included driving transducer (14), as seen in FIGS. 5a through 5c, is placed in housing (7) adjacent to imaging array (6) at a location that preferably places it over the attachment point line of the manubrium during most examinations. Synchronization of the drive transducer signal with imaging array (6) permits detailed sampling of the periodic motions of the middle and inner ear structures induced by periodic signals applied by drive transducer (14), continuous wave, pulsed, or otherwise modulated signals. Accordingly, as shown in FIGS. 5a, 5b and 5c, a single, low frequency crystal or array transducer (14) for introduction of drive signals in the audible, sub-audible, or super-audible frequency ranges may be included in otoscope (100). High-power ultrasonic transducer (14) may also be used for ultrasonic cleaning of middle ear surfaces, ultrasonic cleaning of ossicles, or ultrasound tissue damage and/or removal for the purpose of ultrasound surgery within the middle and inner ear. The high powered transducer (14), when used for ultrasonic cleaning or surgery, must be positioned in the probe tip such that it is not placed over a portion of the tympanum containing the manubrium when the imaging transducer is properly positioned. An optional means to adjust the position between the imaging transducer (6) and high powered transducer (14) can be provided. The high powered transducer (14) is shown angled toward the image plane of the imaging transducer in FIG. 5a. This is to permit imaging of the site being cleaned or ablated. Optional angular adjustment of the high powered, drive, (14) and imaging transducers (6) can be provided. Ultrasound otoscope probe (100), with its integral audible and near-audible frequency drive/surgical transducer, is ideally suited for the detection of pathological tissue growth on the stapes, as seen in patients with otosclerosis, and for dynamic studies of the ossicles. It is therefore, similar to ultrasound surgery transducers. However, devices used for surgery are typically operated at their center frequency and have narrower bandwidths to maximize the transfer of energy at frequencies known to produce tissue damage. These transducers are more sensitive and can deliver more energy and deliver this energy at the frequencies that are optimally suited to induce tissue damage. Their wider bandwidth drive transducer counter parts are more optimally suited to and designed for driving the middle and inner ear structures, at lower acoustic energy output levels, over range of frequencies from about 1 Hz to 60 Hz. Typical narrow band transducers may have a −6 dB percent bandwidth of from 10% to 30%. A drive transducer with its resonant frequency centered in the 1 Hz to 60 Hz range would have a % Bandwidth of about 200%. The drive transducer is however best designed to operate well out of its resonance frequencies to achieve more controllable acoustic energy output over the frequency range required. It is possible and preferred that one transducer is used for both high power (ultrasound cleaning and surgery) and for drive (dynamic studies) transducer applications. The transducer will operate at its resonance frequency for high powered applications and well away from its resonant frequency for drive transducer applications.

To conclude, the invention is comprised of filling an air-filled cavity, the middle ear, with fluid and placing a small amount of fluid or coupling gel in the external ear Then a very thin shaft (9) and an integral imaging array (6) at its end are inserted into the external ear canal. The imaging array and any included drive transducer are coupled to the tympanum with coupling fluid or gel.

To further facilitate the invention and its usage, enhancements to the invention may include the following.

1) Offsetting the image array (6) from the center of the transducer probe housing tip.
2) Including the ability to tilt the imaging array (6) and drive transducer (14) if included, under user or system control for the purpose of 2D image plane optimization or 3D data acquisition.
2) Use of planar or curved imaging arrays.
3) Use of 2D imaging arrays.
4) Use of synthetic aperture techniques or any of its variants.
5) Incorporation of a separate transducer for use in ultrasound cleaning or surgery.

What is claimed is:

1. An ultrasonic imaging device comprising:

a shaft having a central longitudinal axis and a distal end, the shaft having generally an "L" shape such that the distal end is offset from the central longitudinal axis;

an ultrasonic imaging array movably associated with the shaft, wherein the shaft is adapted to be inserted the external portion of the ear and adapted for imaging the middle and inner ear.

2. The device of claim 1, wherein: the shaft is plastically deformable and adapted to bend around corners.

3. The device of claim 1, wherein:

the imaging array is offset from the shaft and slants away from the shaft such that the plane of the shaft and the plane of the array form an angle therebetween.

4. The device of claim 2, wherein:

there is a narrowing defined between the array and the shaft to limit fatigue and failure of the device as the array is bent with respect to the shaft to achieve various elevation and azimuthal angular deflections.

5. The device of claim 1, wherein:

the shaft houses electronic interconnects originating from the array.

6. The device of claim 1, further comprising a plastically deformable support extending beyond said shaft and having a mounting surface for the array, the shaft being an integral part of a flexible casing which surrounds and hermetically seals the deformable support and the array within the casing.

7. The device of claim 1, wherein:

the ultrasonic imaging array is a two-dimensional array.

8. The device of claim 6, wherein:

the mounting surface is bent such that the bend permits the ultrasonic imaging array to slip under the ridge of the external auditory canal.

9. An ultrasonic imaging device comprising:

a shaft having a central longitudinal axis and a distal end, the shaft having generally an "L" shape such that the distal end is offset from the central longitudinal axis;

an ultrasonic imaging array movably associated with the shaft; and a drive transducer for introduction of drive signals in the audible, sub-audible, and super-audible frequency ranges, located adjacent to the ultrasonic imaging array, wherein the distal end of the shaft is adapted to be inserted the external portion of the ear and adapted for imaging the middle and inner ear.

10. The device of claim 6, wherein:

the mounting surface attaches to the deformable support using machined joints.

11. The device of claim 6, further comprising:

means for automatically controlling the position of the mounting surface.

12. A method for ultrasonic imaging, comprising;

flooding a body cavity filled with air with an acoustically conductive fluid to gain acoustic access to an are to be imaged within or opposite the body cavity from a later inserted imaging array;

applying an additional volume of acoustically conductive fluid to tissues covering the body cavity inserting an ultrasonic probe containing the imaging array into the area adjacent to the body cavity into which or through which imaging is to be conducted; and taking an ultrasonic image of the area to be imaged through at least part of the body cavity with the imaging array.

13. The method of claim 12, wherein:

the areas to be imaged is a middle or inner human ear and the body cavity is the middle ear.

14. The method of claim 13, wherein:

the area to be imaged is imaged through the tympanum of the human ear.

15. An array probe comprising:

a probe body having a central longitudinal axis, the probe body having a distal end, the probe body having generally an "L" shape such that the distal end is offset from the central longitudinal axis;

an imaging array attached to the distal end, wherein the array is adapted to be inserted into the external ear and adapted for the purpose of imaging the middle and inner ear.

16. The probe of claim 15, wherein the probe body is plastically deformable and the imaging array is movable in the azimuthal and elevational directions.

17. The probe of claim 15, wherein the array is offset from the longitudinal axis.

18. The probe of claim 16 wherein the probe body is comprised of a plastically deformable support extending parallel to the longitudinal axis and associated with the array, and a flexible envelope surrounding the support shaft and the array and containing a lens therein.

19. A method for viewing the internal and middle ear comprising the steps of:

filling the middle ear cavity with fluid;

placing enough fluid in the external ear cavity for acoustic coupling;

inserting a probe into the external ear for the purpose of imaging the middle and inner ear, the probe having a central longitudinal axis and a dimension of less than 8 mm and an imaging array movably mounted in the azimuthal and elevational direction on the distal end of the probe, the array being offset from the longitudinal axis.

20. The method of claim 19 wherein the array is one dimensional and further comprising the step of sweeping a two-dimensional image plane in the ear scannable with the one-dimensional array to collect data sets for a three-dimensional image by movement in the elevation direction of the array.

21. The device of claim 1, wherein:

a high powered transducer for ultrasonic cleaning and/or surgery of middle and inner ear tissues is located adjacent to the ultrasonic imaging array.

22. The device of claim 1, wherein:

a transducer for introduction of drive signals in the audible, sub-audible, or super-audible frequency ranges and for ultrasonic cleaning and/or surgery of middle and inner ear tissues is located adjacent to the ultrasonic imaging array.

23. The device of claim 22 wherein the transducer is two transducers, one a high powered transducer and the other a drive transducer.

24. The device of claim 9 wherein the drive transducer can have continuous wave, pulsed wave, or otherwise modulated signals operated synchronously with the imaging array which is connected to an imaging system driving both the drive and imaging transducers in variable or fixed point synchrony.

25. The method of claim 20, wherein a drive transducer is included in the probe, the method further comprising the step of using the drive transducer to drive the middle and inner ear structures.

26. A probe having:

a support structure having a first portion and an end connected to the first portion, the first portion and the end forming together in one view, a generally "L" shape such that the end is offset from the first portion;

an ultrasonic imaging array connected to the first portion, wherein the L shape of the support structure enables the array to be slipped under the ridge in the anterior wall of the external auditory canal and to the side of the manubrium of the malleus which blocks the acoustic path down the midline of the tympanum of an ear.

27. The probe of claim 26 wherein the first portion is plastically deformable.

28. The probe of claim 27 wherein the end is movable with respect to the end portion such that it may be swiveled with respect to the first portion.

29. The probe of claim 28, wherein the support structure is encased in a flexible envelope with the end portion being mounted in an off center position with respect to the central longitudinal axis of the envelope.

30. The probe of claim 28 having a widest dimension of between about 3 mm and about 8 mm.

31. The probe of claim 30 having a narrowest dimension of between about 2 mm and about 6 mm.

32. A probe having:

a support structure having a first portion and an end connected to the first portion, the first portion and the end forming together in one view, a generally "L" shape such that the end is offset from the first portion;

an ultrasonic imaging array connected to the first portion, wherein the probe will image through a cavity from outside the cavity.

* * * * *

UNITED STATES PATENT AND TRADEMARK OFFICE
CERTIFICATE OF CORRECTION

PATENT NO. : 6,093,150
DATED : July 25, 2000
INVENTOR(S) : Paul E. Chandler et al.

Page 1 of 2

It is certified that error appears in the above-identified patent and that said Letters Patent is hereby corrected as shown below:

Title page,
Before line 1, under "U.S. PATENT DOCUMENTS", insert the following:
-- 4,561,446    12/1985    Hetz
   4,605,009    08/1986    Pourcelot et al.
   4,917,097    04/1990    Proudian, deceased et al.
   5,126,616    06/1992    Gorton et al.
   5,131,396    07/1992    Ishiguro et al.
   5,161,537    11/1992    Hashimoto et al. --

After line 1, under "U.S. PATENT DOCUMENTS", insert the following:
-- 5,176,141    01/1993    Bom et al. --.

After line 11, insert the following:
-- M.C. Oehler et al. "Magnetic Susceptibility Artifacts on High-Resolution MR of the Temporal Bone". *AJNR Am. J. Neuroradiol*, 16: pgs. 1135-1143, May 1995.

D. S. Poe et al. "INTRAVENOUS FLUORESCEIN FOR DETECTION OF PERILYMPHATIC FISTULAS". *The American Journal of Otology*/vol. 14, No. 1: pgs. 51-55, January 1993.

Q. M. Ali et al. "Three-dimensional CT of the middle ear and adjacent structures". *Neuroradiology* (1993) 35; pgs 238-241.

I. D. Bottrill et al. "ENDOSCOPED-ASSISTED EAR SURGERY". *The American Journal of Otology*/Volume 16, Number 2: pgs. 158-163, March 1995.

O. Delaroche et al. "Perilymph detection by beta 2-transferrin immunoblotting assy. Application to the diagnosis of perilymphatic fistulae." *Clin. Chim Acta* 1996 February 9; 245(1) :93-104. --.

Column 2,
Line 28, change "giver" to -- given --.

Column 5,
Line 15, change "elevation, and" to -- "elevation" and --.

UNITED STATES PATENT AND TRADEMARK OFFICE
CERTIFICATE OF CORRECTION

PATENT NO. : 6,093,150
DATED : July 25, 2000
INVENTOR(S) : Paul E. Chandler et al.

It is certified that error appears in the above-identified patent and that said Letters Patent is hereby corrected as shown below:

Column 7,
Line 62, change "is the" to -- to the --.

Claim 1,
Line 6, change "inserted the" to -- inserted into the --.

Claim 9,
Line 11, change "inserted the" to -- inserted into the --.

Claim 12,
Line 3, change "an are" to -- an area --.

Signed and Sealed this

Eighteenth Day of December, 2001

Attest:

*Attesting Officer*

JAMES E. ROGAN
*Director of the United States Patent and Trademark Office*